US006452371B1

(12) United States Patent
Brugger

(10) Patent No.: US 6,452,371 B1
(45) Date of Patent: Sep. 17, 2002

(54) DIFFERENTIAL CONDUCTIVITY HEMODYNAMIC MONITOR

(75) Inventor: James M Brugger, Boulder, CO (US)

(73) Assignee: Gambro, Inc., Lakewood, CO (US)

( * ) Notice: Subject to any disclaimer, the term of this patent is extended or adjusted under 35 U.S.C. 154(b) by 0 days.

(21) Appl. No.: 09/563,107

(22) Filed: May 2, 2000

Related U.S. Application Data

(63) Continuation of application No. 09/220,139, filed on Dec. 23, 1998, now Pat. No. 6,075,367, which is a continuation of application No. 08/876,445, filed on Jun. 16, 1997, now Pat. No. 5,900,726, which is a continuation of application No. 08/486,982, filed on Jun. 7, 1995, now Pat. No. 5,644,240, which is a continuation-in-part of application No. 08/332,647, filed on Nov. 1, 1994, now Pat. No. 5,510,716, which is a continuation of application No. 07/954,584, filed on Sep. 30, 1992, now abandoned.

(51) Int. Cl.[7] .................. G01N 27/00; G01N 27/02; A61M 1/00; G01F 1/74; B01D 11/00

(52) U.S. Cl. ............... 324/71.1; 324/439; 324/445; 324/450; 604/30; 604/65; 604/646; 604/4; 73/861.04; 73/861.07; 73/861.08; 210/96.1; 210/646

(58) Field of Search .............. 324/71.1, 425, 324/439, 692, 705, 445, 444, 450; 210/96.1, 646; 73/861.07, 861.08, 861.04; 436/150; 604/30, 65, 246, 4

(56) References Cited

U.S. PATENT DOCUMENTS

| | | | |
|---|---|---|---|
| 2,709,785 A | 5/1955 | Fielden | 324/701 |
| 3,324,720 A | 6/1967 | Sutherland | 73/861.07 |
| 3,396,331 A | 8/1968 | Sperry, III | 324/445 |
| 3,404,336 A | 10/1968 | Rosenthal | 324/445 |
| 3,450,984 A | 6/1969 | Holmes | 205/794.5 |
| 3,482,575 A | 12/1969 | Claff et al. | 604/6.14 |

(List continued on next page.)

FOREIGN PATENT DOCUMENTS

| | | |
|---|---|---|
| EP | 0 097 366 | 1/1984 |
| EP | 0 272 414 | 6/1988 |
| ES | 2026508 | 5/1992 |
| GB | 2093192 | 8/1982 |
| JP | 36990/77 | 10/1977 |
| JP | 190873/85 | 9/1985 |
| SU | 521891 | 10/1976 |
| SU | 1013853 | 4/1983 |

OTHER PUBLICATIONS

Robert L. Hester, Ph.D., "A New Technique for Determining Recirculation in the ESRD Patient", Nephrology News & Issues, pp. 44–55, Jun. 1993, Jackson, MS.

Gambro, "FAM 10 Fistula Flow Studies and Their Interpretation", pp. 1–31, Lund Sweden, published on or before Sep. 29, 1991.

Salamon et al. Translation: low frequency electrodeless conductometer for measuring the electrical conductivity of solutions, 1959, Industrial Group Headquarters, Risley, Warrington, Lancashire, GB.

(List continued on next page.)

*Primary Examiner*—N. Le
*Assistant Examiner*—Wasseem H. Hamdan
(74) *Attorney, Agent, or Firm*—Edna M. O'Connor; Peter B. Scull; Laura M. Butterfield

(57) ABSTRACT

A flow rate of a fluid flowing in a tube is quantitatively determined by altering the electrical conductivity of the fluid by injection of a bolus of saline. The electrical conductivity of the altered conductivity is measured over the time it takes the altered conductivity fluid to pass a conductivity measuring location. The measured conductivity is integrated over the time it takes to pass the conductivity measuring location. The integral is interpreted to determine the flow rate.

20 Claims, 7 Drawing Sheets

U.S. PATENT DOCUMENTS

| | | | |
|---|---|---|---|
| 3,491,592 A | 1/1970 | Evers et al. | 73/861.07 |
| 3,619,423 A | 11/1971 | Galletti et al. | 210/632 |
| 3,722,276 A | 3/1973 | Chandler et al. | 73/861.07 |
| 3,867,688 A | 2/1975 | Koski | 324/445 |
| 3,980,946 A | 9/1976 | Fleury | 324/445 |
| 4,081,372 A | 3/1978 | Atkin et al. | 210/94 |
| 4,136,563 A | 1/1979 | Mueller et al. | 73/861.03 |
| 4,138,639 A | 2/1979 | Hutchins | 324/442 |
| 4,181,610 A | 1/1980 | Shintani et al. | 210/85 |
| 4,361,049 A | 11/1982 | Volgyesi | 73/861.05 |
| 4,508,622 A | 4/1985 | Polaschegg et al. | 210/96.2 |
| 4,650,458 A | 3/1987 | Dahlberg et al. | 604/6.06 |
| 4,739,492 A | 4/1988 | Cochran | 702/150 |
| 4,740,755 A | 4/1988 | Ogawa et al. | 324/445 |
| 4,825,168 A | 4/1989 | Ogawa et al. | 324/439 |
| 4,995,268 A | 2/1991 | Ash et al. | 73/861.05 |
| 5,004,459 A | 4/1991 | Peabody et al. | 604/29 |
| 5,092,836 A | 3/1992 | Polaschegg | 604/6.11 |
| 5,312,550 A | 5/1994 | Hester | 210/646 |
| 5,453,576 A | 9/1995 | Krivitski | 600/481 |
| 5,510,716 A | 4/1996 | Buffaloe IV, et al. | 324/445 |
| 5,510,717 A | 4/1996 | Buffaloe IV, et al. | 324/445 |
| 5,595,182 A | 1/1997 | Krivitski | 600/505 |
| 5,685,989 A | 11/1997 | Krivitski et al. | 210/646 |

OTHER PUBLICATIONS

Richard A. Sherman, "Recirculation Revisited", Seminars in Dialysis, vol. 4, No. 4, pp. 221–223, Oct.–Dec. 1991, New Jersey.

McKamy SMith, "Cardiac Output Determined by the Saline Conductivity Method Using an Extraarterial Conductivity Cell", Cardiovascular Research Center Bulletin, vol. 5, No. 4, pp. 123–134, Apr.–Jun. 1967, Texas.

Mogens Thomsen et al., "Evaluation of Clinical Examination Preceding Surgical Treatment of AV–Fistula Problems," Acta Chir Scand, vol. 151, pp. 133–137, 1985, Sweden.

Transonic Systems, Inc., Access Flow & Recirculation Measured During Hemodialysis, Oct. 1994, N. Y.

C. Aldridge et al., "The Assessment of Arteriovenous Fistulae Created for Haemodialysis from Pressure and Thermal Dilution Measurements, Journal of Medical Engineering & Technology," vol. 8, No. 3, pp. 118–124, May/Jun. 1984, U.K.

C. Aldridge, et al., "Instrument Design for the Bedside Assessment of Arteriovenous Fistulae in Haemodialysis Patients," Proceedings EDTNA–ERCA, vol. 14, pp. 255–260, 1985, U.K.

C. Aldridge, "The Use and Management of Arteriovenous Fistulae Fact and Fiction", EDTNA ERCA, Journal SVII–4, pp. 29–35, Oct. 1991, United Kingdom.

Joseph J. Carr, "Integration of Decaying Exponential Sensor Output Signals", Sensors, pp. 28–34, Jul. 1989, Virginia.

J. Daugirdas, "The Fourth Annual Advanced Dialysis Technical Symposium", Dialysis & Transplantation, vol. 17, No. 8, pp. 432–433, Aug. 1988, Illinois.

Fresenius, "BTM 4008", Nov. 1993, Germany and translation from German to English.

Gambro, "Fistula Assessment monitor FAM 10," approximately 1985, U.K.

Gambro, "Fistula Assessment Monitor FAM 10 Operator's manual," approximately 1985, U.K.

Gambro, "Fistula Assessment Monitor FAM 10 Service Manual," approximately 1985, Sidcup, Kent, U.K.

J.S. Gani et al., "Use of the Fistula Assessment Monitor to Detect Stenoses in Access Fistulae," (abstract) Australian Society of nephrology, 1989, Australia.

Jonathan S. Gani, "Use of the Fistula Assessment Monitor to Detect Stenoses in Access Fistulae," American Journal of Kidney Diseases, vol. XVII, No. 3, pp. 303–306, Mar. 1991, Newcastle, Australia.

R N Greenwood et al. "Assessment of Arteriovenous Fistulae from Pressure and Recirculation Studies. Clinical Experience in 186 Fistulae", Abstract, p. 106, 1985, London, U.K.

R N Greenwood et al., "Assessment of Arteriovenous Fistulas From Pressure and Recirculation Studies: Clinical Experience in 215 Upper Limb Fistulas, EDTA–ERA," vol. 22, pp. 296–302, 1985, London, U.K.

R N Greenwood et al., "Assessment of Arteriovenous Fistulae from Pressure and Thermal Dilution Studies: Clinical Experience in Forearm Fistulae," Clinical Nephrology, vol. 23, No. 4, pp. 189–197, 1985, U.K.

L. Goldstein et al., The Assessment of Arteriovenous Fistulae From Pressure and Recirculation Studies:, Porc EDT-NA–ERCA, vol. 14, pp. 207–215, 1985, United Kingdom.

Lynn W. Hart et al., A Noninvasive Electromagnetic Conductivity Sensor for Biomedial Applications:, IEEE Transactions on Biomedical Engineering, vol. 35, No. 12, pp. 1011–1022, Dec. 1988, Maryland.

Robert L. Hester et al., "The Determination of Hemodialysis Blood Recirculation Using Blood urea nitrogen Measurements", American Journal of Kidney Diseases, vol. XX, No. 6, pp. 598–602, Dec. 1992, Mississippi.

R.L. Hester et al., "Non–Invasive measurement of Recirculation in the Dialysis Patient", Abstract No. 7, Jul. 1992.

Robert L. Hester et al., "Non–Invasive Determination of Recirculation in the Patient on Dialysis," ASAIO Journal, pp. M190–M193, 1992, Mississippi.

M. Kramer et al., "Automated measurement of Recirculation," EDTNA–ERCA, Journal, vol. XIX, No. 2, Apr. 1993.

Matthias Kramer et al., "A Device for Control of Thermal Parameters and Recirculation Measurement in hemodialysis," Nov., 1992, Germany.

Transonic Systems, Inc., "Transonic Hemodialysis Monitor Measures Access Flow Recirculation Cardiac Output Routinely during Dialysis", Apr. 1995.

Nikolai M. Krivitski, "Novel Method to Measure Access Flow During Hemodialysis by Ultrasound Velocity Dilution Technique", Jul. 27, 1995, ASAIO Journal, pp. 0014–0018.

Thomas A. Depner and Nikolai M. Krivitski, "Clinical Measurement of Blood Flow in Hemodialysis Access Fistulae and Grafts by Ultrasound Dilution", Jul. 27, 1995, ASAIO Journal, pp. 0018–0022.

Thomas A. Depner et al., "Hemodialysis Access Recirculation Measured by Ultrasound Dilution", Jul. 27, 1995, ASAIO Journal, pp. 0022–0026.

N.M. Krivitski, "Novel Method to Measure Access Flow During Hemodialysis by Ultrasound Dilution (UD)", ASAIO Journal 1995.

Nikolai M. Krivitski, "Theory and Validation of Access Flow Measurement by Dilution Technique during Hemodialysis", Kidney International, vol. 48 (1995), pp. 244–250.

N.M. Krivitski, "Accuracy of Ultrasound Dilution Method to Measure Access Flow (AF) in Hemodialysis", XIIIth International Congress of Nephrology, Abstract, 1995.

Nikolai Krivitski, Ph.D. "New Method to Measure Recirculation (Rc) and Access Flow During Hemodialysis (HD)" American Nephrology Nurses' Association 26th National Symposium Exhibitor Continuing Education Program, Abstract, 1995.

T. Depner, "Changes in Access Blood Flow (Qac) and Appearance of Recirculation (RC) During Hemodialysis", XIIIth International Congress of Nephrology, Abstract, 1995.

T.A. Depner et al., "Hemodialysis Access Recirculation (Rc) Measured by Ultrasound Dilution", ASAIO Journal 1995 Abstracts, Supplement to Jan.–Mar. 1995 vol. 41, No. 1, p. 80.

T.A. Depner and N.M. Krivitski, "Clinical Measurement of Blood Flow in Hemodialysis Access Fistulae and Grafts by Ultrasound Dilution", ASAIO Journal 1995 Abstrats, Supplement to Jan.–Mar. 1995 vol. 41, No. 1, p. 80.

Transonic Systems Inc., "Recirculation, Access Flow Measurements", 1995, pp. 19–26.

N.M. Krivitski, "Cardia Output Measurement in Extracorporeal Systems by Ultrasound Velocity Dilution", ASAIO Abstracts, 1994, p. 82.

Jeffrey Sands et al., "The Effect of Doppler Flow Screening Studies and Elective Revisions on Dialysis Access Failure", Reprint from ASAIO Transactions, Jul.–Sep., 1992, pp. M524–M527.

John L. Nosher, Death Taxes, and Vascular Access Dysfunction, Seminars in Dialysis, vol. 4, No. 2, pp. 67–68, Apr.–Jun. 1991, New Jersey.

In–Lin Diagnostics (brochure) "Improve the Clinical Outcome of Every Patient!", four pages, (undated).

In–Line Diagnostics (brochure) "Non–Invasive Blood Volume Monitoring", two pages, 1994.

In–Line Diagnostics (brochure) "The Crit–Line System", two pages, (undated).

John D. Bower and Thomas G. Coleman, "Circulatory Function During Chronic Hemodialysis", vol. XV Trans. Amer. Soc. Artif. Int. Organs, 1969, pp. 373–377.

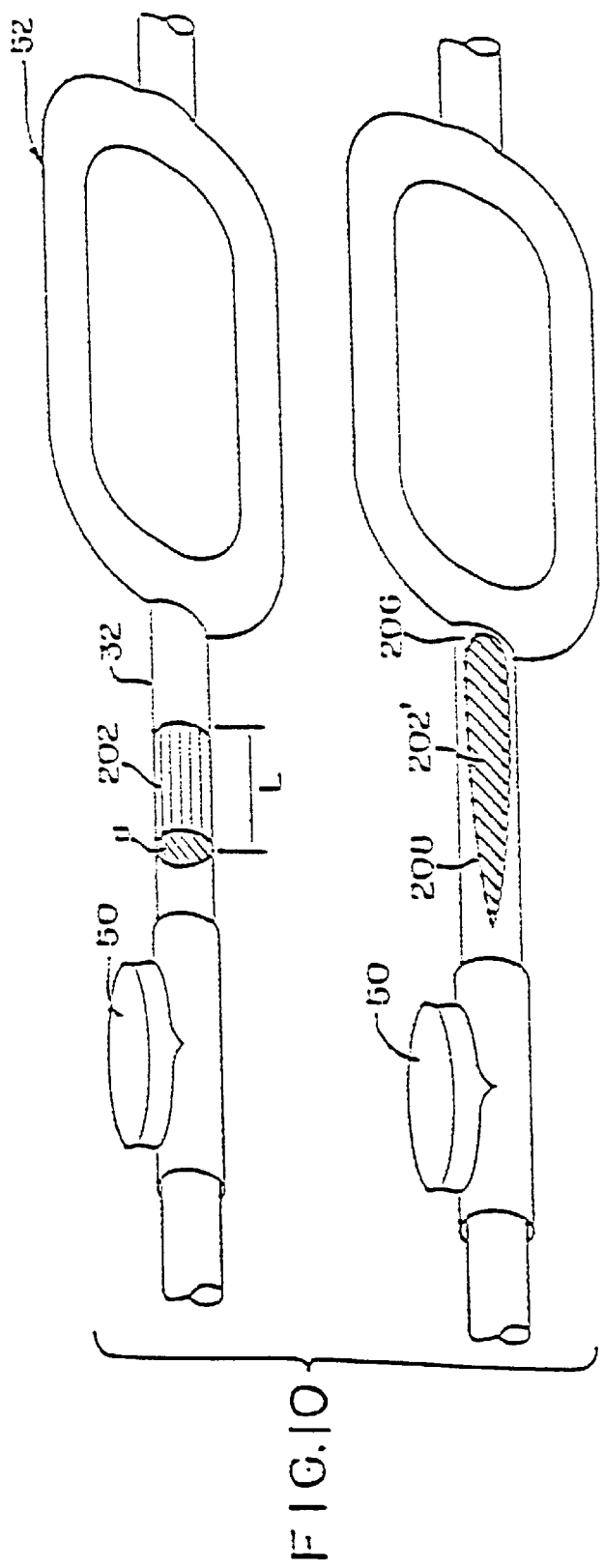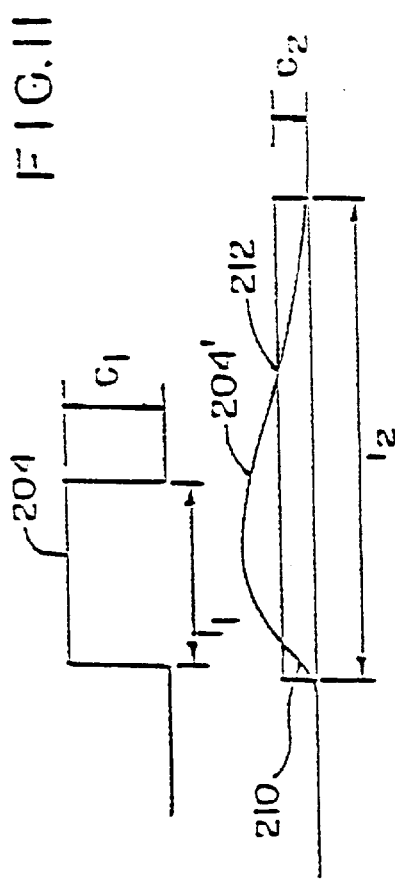

DIFFERENTIAL CONDUCTIVITY HEMODYNAMIC MONITOR

RELATED APPLICATIONS

This application is a continuation of U.S. patent application Ser. No. 09/220,139 filed Dec. 23, 1998, now U.S. Pat. No. 6,075,367; which is a continuation of U.S. patent application Ser. No. 08/876,445 filed Jun. 16, 1997, now U.S. Pat. No. 5,900,726; which was a continuation of U.S. patent application Ser. No. 08/486,982 filed Jun. 7, 1995, now U.S. Pat. No. 5,644,240; which was a continuation-in-part of U.S. patent application Ser. No. 08/332,647 filed Nov. 1, 1994, now U.S. Pat. No. 5,510,716; which was a continuation of U.S. patent application Ser. No. 07/954,584 filed Sep. 30, 1992, now abandoned.

FIELD OF THE INVENTION

This invention relates to measurement of multiple hemodynamic variables. More particularly, this invention relates to measurement of the hemodynamic variables during a medical procedure or for diagnostic purposes using a differential conductivity monitor to measure or detect at least one of recirculation efficiency, flow rate or the presence of air bubbles.

BACKGROUND OF THE INVENTION

In many medical situations it is desirable to quantitatively determine, or measure, various hemodynamic parameters, such as the recirculation rate or the recirculation efficiency of a biological or medical fluid to increase the benefits of, or decrease the time required for, a therapeutic treatment, or for diagnostic purposes. For example, hemodialysis (herein "dialysis") is an inconvenient, expensive, and uncomfortable medical procedure. It is, therefore, widely recognized as desirable to minimize the amount of time required to complete the procedure and to achieve a desired level of treatment.

In dialysis, a joint is typically surgically created between a vein and an artery of a patient undergoing dialysis. The joint provides a blood access site where in inlet line to a dialysis apparatus and an outlet line from the dialysis apparatus are connected. The inlet line draws blood to be treated from the patient, while the outlet line returns treated blood to the patient.

The joint may be an arteriovenous fistula, which is a direct connection of one of the patient's veins to one of the patient's arteries. Alternatively the joint may be a synthetic or animal organ graft connecting the vein to the artery. As used herein, the term "fistula" refers to any surgically created or implanted joint between one of the patient's veins and one of the patient's arteries, however created.

In the fistula a portion of the treated blood returned to the patient by the outlet line may recirculate. Recirculating treated blood will co-mingle with untreated blood being withdrawn from the patient by the inlet line. This recirculation, and the resulting co-mingling of treated an untreated blood, is dependent, in part, on the rate at which blood is withdrawn from and returned to the patient. The relationship is typically a direct, but non-linear relationship. It can be readily appreciated that the dialysis apparatus will operate most effectively, and the desired level of treatment achieved in the shortest period of time, when the inlet line is drawing only untreated blood at the maximum flow rate capability of the dialysis apparatus consistent with patient safety. As a practical matter, however, as flow rate through the dialysis apparatus is increased, the proportion of recirculated treated blood in the blood being drawn through the inlet line is increased. In order to select the flow rate through the dialysis apparatus, it is desirable to know proportion of recirculated treated blood in the blood being withdrawn from the patient by the inlet line. This proportion is referred to herein as the "recirculation ratio". The recirculation ratio can also be defined as the ratio between the flow of recirculated blood being withdrawn from the fistula to the flow of blood being returned to the fistula. Recirculation efficiency may then be defined by the relationship.

$$E = 1 - R \text{ (Equation 1)}$$

where
  E=Recirculation efficiency
  R=Recirculation ratio

Alternatively, recirculation efficiency way be equivalently expressed as the ratio of blood flow being returned to the fistula, but not being recirculated, to the total blood flow being returned to the fistula. Knowing the recirculation efficiency, the dialysis apparatus operator can adjust the flow rate through the dialysis apparatus to minimize the time required to achieve the desired level of treatment.

In the prior art, quantitative determination of recirculation ratio or recirculation efficiency has typically required laboratory testing, such as blood urea nitrogen tests, which take considerable amounts of time and which require withdrawing blood from the patient, which is recognized as undesirable.

A method and apparatus for qualitatively detecting the presence or absence of recirculation in a fistula is described in "FAM 10 Fistula Flow Studies and their Interpretation" published by Gambro, Ltd. based on research performed in 1982. The Gambro method and apparatus injects a quantity of a fluid having an optical density less than the optical density of treated blood into the dialysis apparatus outlet line. A resulting change in the optical density of the blood being drawn through the dialysis apparatus inlet line is qualitatively detected as indicative of the presence of recirculation. The Gambro method and apparatus does not quantitatively determine or measure a recirculation ratio or recirculation efficiency.

Devices which qualitatively determine recirculation by thermal techniques are also known.

A quantitative measurement of the recirculation efficiency of a bodily or medical fluid is useful in other therapeutic and diagnostic procedures as well. For example, recirculation ratios and efficiencies are useful for determining cardiac output, intervascular recirculation, recirculation in non-surgically created access sites, and dialyzer performance from either the blood side or the dialysis side of the dialyzer, or both.

It is known that the electrical conductivity of a fluid in a closed non-metallic conduit can be measured without contact with the fluid by inducing an alternating electrical current in a conduit loop comprising a closed electrical path of known cross sectional area and length. The magnitude of the current thus induced is proportional to the conductivity of the fluid. The induced current magnitude may then be detected by inductive sensing to give a quantitative indication of fluid conductivity. A conductivity cell for measuring the conductivity of a fluid in a closed conduit without contact with the fluid is described in U.S. Pat. No. 4,740,755 entitled "Remote Conductivity Sensor Having Transformer Coupling In A Fluid Flow Path," is issued Apr. 26. 1988 to Ogawa and assigned to the assignee of the present invention, the disclosure of which is hereby incorporated herein by reference.

It is further desirable to have a way of detecting the presence of air in a dialysis apparatus outlet line to minimize the probability of air being returned to a patient in the outlet line. It is further advantageouis to have a means of determining a volume flow rate of fluid flowing in the inlet and outlet tube of the dialysis apparatus.

Air bubble detectors which detect the presence of an air bubble soncially, ultrasonically or optically are knwon, but a more sensitive device that is not subject to sonic or optical shadows or distortion is desirable.

It is further desirable to measure a flow rate of a fluid in a tube, either as a part of a recirculation monitoring procedure, or as a separately measured hemodynamic parameter.

It is still further desirable to provide a hemodynamic monitoring device which is capable of monitoring more than one hemodynamic parameter, in order to reduce system cost and increase system flexibility.

It is against this background that the differential conductivity hemodynamic monitor of the present invention developed.

SUMMARY OF THE INVENTION

A significant aspect of the present invention is a method and an apparatus for accurately measuring a volumetric flow rate of a fluid flowing in a tube. In accordance with this aspect of the invention the fluid has an electrical conductivity and a corresponding concentration of conductivity producing ions. The electrical conductivity of the fluid is altered, as by injection of a bolus of hypertonic saline solution. The altered electrical conductivity is measured and integrated over time. The integrated value is then interpreted to determine flow rate.

Further in accordance with this apsect of the invention, fluid conductivity is measured by flowing the fluid through a conductivity cell with a continuous path configuration, inducing an electrical current in the fluid in the conductivity cell, and sensing the first electrical current in the first fluid in the first conductivity cell. Still further in accordance with this aspect of the invention, current inducing and sensing may be performed by positioning an exciting electromagnetic coil in proximity with the conductivity cell to induce the electrical current in the continuous path of the conductivity cell, and positioning a sensing electromagnetic coil in proximity with the conductivity cell to sense the induced current. Yet further in accordance with this aspect of the invention, the effects of background conductivity are compensated for.

Still further in accordance with this aspect, a second fluid may be flowing in another tube, and the conductivity measuring may measure the difference between the conductivity of the first fluid in the tube and the conductivity of the second fluid in the other tube.

A further significant aspect of the present invention is an apparatus capable of performing a plurality of hemodynamic parameter determinations. In accordance with this aspect of the invention the apparatus measures the flow rate of a fluid in a tube and further is suitable for use as a recirculation monitor for determining a degree of recirculation of a fluid in a zone of a vessel.

BRIEF DESCRIPTION OF THE DRAWINGS

FIG. 10 is a diagrammatic representation of the passage of an ideal bolus of saline and an actual bolus of saline through a conductivity cell of the present invention.

FIG. 11 is an illustration of the output signals from the conductivity cell of FIG. 10.

DETAILED DESCRIPTION OF THE PREFERRED EMBODIMENT

Figure 1:
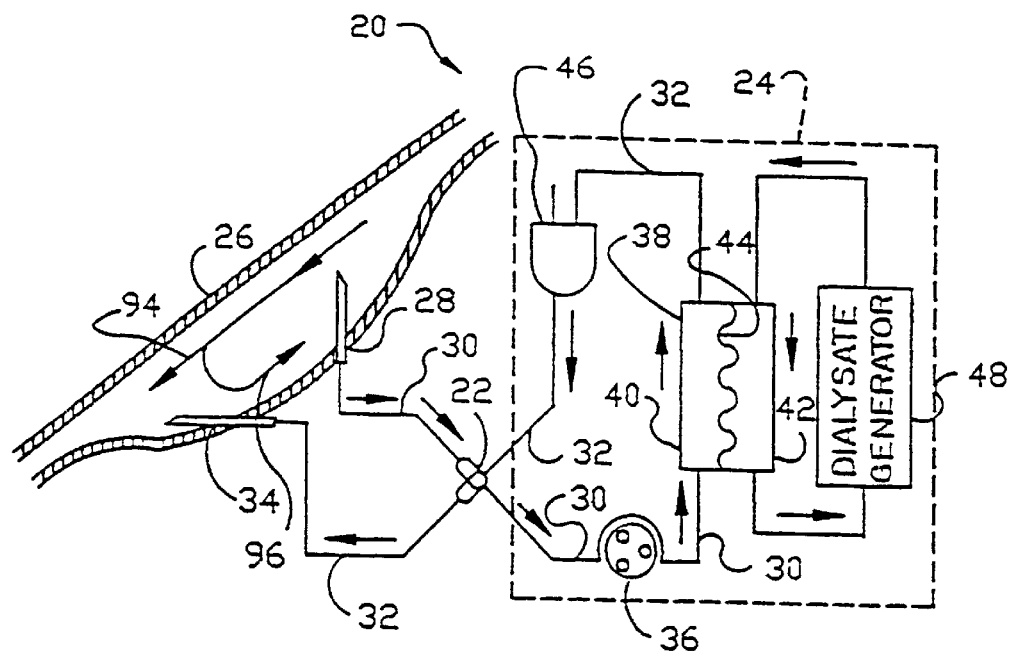
FIG. 1 is a schematic diagram of a dialysis system incorporating a differential conductivity recirculation monitor in accordance with the present invention.

FIG. 1 illustrates a dialysis system 20 incorporating a differential conductivity recirculation monitor 22 for determining and displaying recirculation efficiency in accordance with the present invention. The dialysis system 20, which is one example of a medical system with which the present invention may be advantageously used, comprises a dialysis apparatus 24 connected to a fistula 26 surgically formed in a dialysis patient (not shown). Untreated blood is drawn from the fistula 26 through a dialyzer inlet needle 28 and a dialyzer inlet line 30. Treated blood is returned to the fistula through a dialyzer outlet line 32 and a dialyzer outlet needle 34. The recirculation monitor 22 is located in the dialyzer inlet and outlet lines 30 and 32 at a point intermediate between the fistula 26 and the dialysis apparatus 24.

The dialysis apparatus 24 comprises a blood pump 36 typically a peristaltic pump, a dialyzer 38 having a blood compartment 40 and a dialysate compartment 42 separated by a semi-permeable membrane 44, a bubble trap 46 and a dialysate generator 48. Blood is drawn from the fistula 26 by the action of the blood pump 36 and passed through the blood compartment 40 of the dialyzer 38. The membrane 44 allows transfer of impurities in the blood, such as urea and creatinine, from the blood compartment 40 to the dialysate compartment 42 of the dialyzer 38. The dialysate compartment 42 is connected to dialysate generator 48 which generates the dialysate, a liquid isotonic to blood, and circulates it through the dialysate compartment 42.

Figure 2:
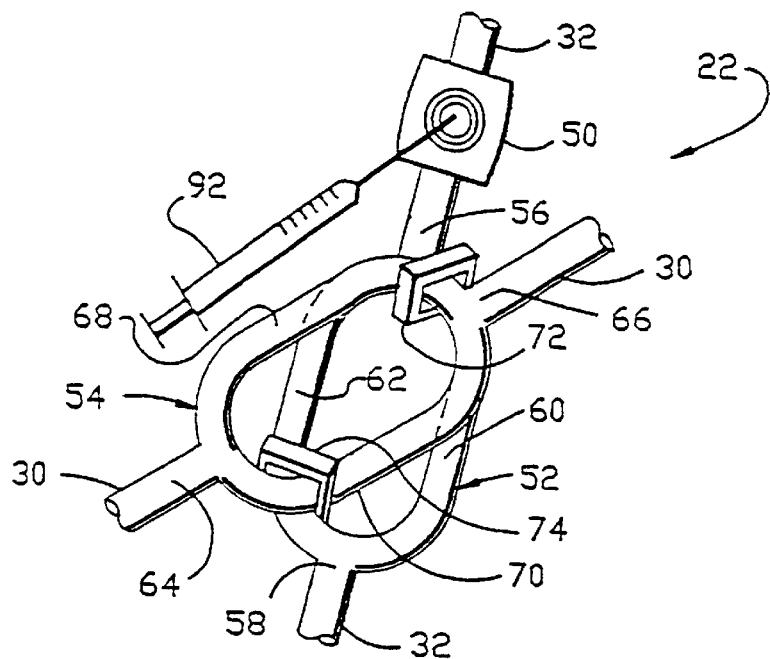
FIG. 2 is a partial perspective view illustrating the functional elements of the differential conductivity recirculation monitor shown in FIG. 1.
Figure 3:
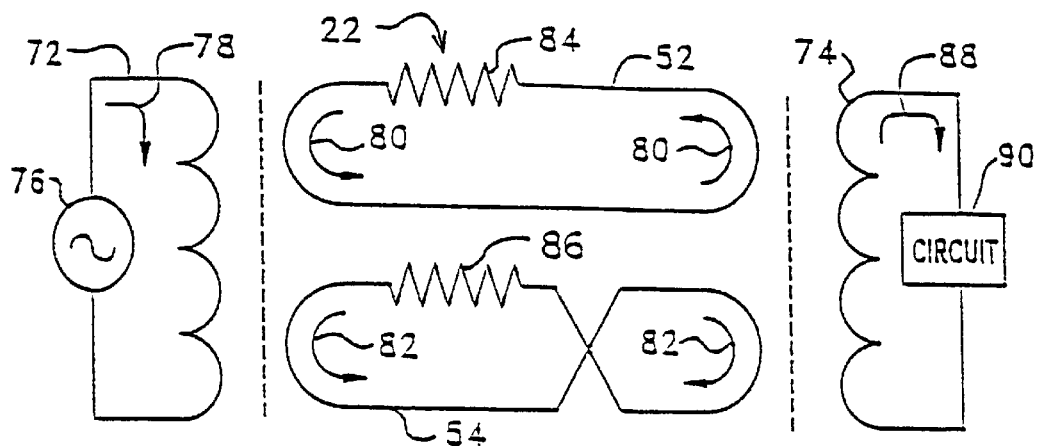
FIG. 3 is an electrical schematic diagram of the differential conductivity recirculation monitor shown in FIG. 2.

The principles of operation of the differential conductivity recirculation detector 22 of the present invention are explained in conjunction with FIGS. 2 and 3. The recirculation detector 22 comprises a needle access site 50 in the dialyzer outlet line 32. A first or outlet conductivity cell 52 is located in the dialyzer outlet line 32 downstream of the needle access site 50. A second or inlet conductivity cell 54 is located in the dialyzer inlet line 30. The first conductivity cell 52 comprises an upstream connection 56, a downstream connection 58 and first and second tubing branches 60 and 62, respectively, each of which interconnect the upstream connection 56 with the downstream connection 58. Treated blood from the dialyzer flows in the dialyzer outlet line 32 through the needle access site 50 to the upstream connection 56. At the upstream connection 56 the flow splits approximately equally with a portion of the treated blood flowing in each of the two tubing branches 60 and 62 of the outlet conductivity cell 52. The flow rejoins at the downstream connection 58 and flows through the dialyzer outlet line 32 to the fistula 26 (FIG. 1). Similarly, the inlet conductivity cell 54 comprises an upstream connection 64, a downstream connection 66 and third and fourth tubing branches 68 and 70, respectively, which each connect the upstream connection 64 to the downstream connection 66. Untreated blood from the fistula 26 flowing in the dialyzer inlet line 30 enters the inlet conductivity cell 54 at the upstream connection 64 divides approximately equally between the third and fourth tubing branches 68 and 70 and rejoins at the downstream connection 66 to the inlet conductivity cell 54. Each one of the tubing branches 60, 62, 68 and 70 has the same cross sectional area and length as each other one of the tubing branches.

The blood, or other biological or medical fluid, flowing in each conductivity cell 52 and 54 comprises an electrical circuit. The electrical circuit is a path for circulation of an electrical current from the upstream connection, through one of the tubing branches, to the downstream connection and from the downstream connection through the other one of the tubing branches to the upstream connection.

The outlet conductivity cell 52 and the inlet conductivity cell 54 are positioned adjacent to each other in an angular relationship resembling a pretzel so that the first tubing branch 60 of the outlet conductivity cell 52 is positioned parallel to the third tubing branch 68 of the inlet conductivity cell at an excitation location. The conductivity cells are further positioned so that the second tubing branch 62 of the outlet conductivity cell 52 crosses the fourth tubing branch 70 of the inlet conductivity cell 54 at an angle, approximately sixty degrees in the preferred embodiment, at a sensing location. An excitation coil 72 encircles the first tubing branch 60 of the outlet conductivity cell 52 and the third tubing branch 68 of the inlet conductivity cell 54 at the excitation location. A sensing coil 74 encircles the second tubing branch 62 of the outlet conductivity cell 52 and the fourth tubing branch 70 of the inlet conductivity cell 54 at the sensing location.

An electrical circuit, as is illustrated schematically in FIG. 3, is thus formed. The excitation coil 72 is inductively coupled to the outlet conductivity cell 52 and the inlet conductivity cell 54. When a source of excitation energy 76 causes an alternating excitation current, illustrated by direction arrow 78, to flow in the excitation coil 72 a changing magnetic field is generated which causes an electrical current, illustrated by the direction arrow 80, to flow in the blood in the outlet conductivity cell 52 and causes another electrical current, illustrated by direction arrow 82, to flow in the same electrical direction in the blood in the inlet conductivity cell 54. Since the conductivity cells 52 and 54 are formed to create electrical paths of equal cross sectional area and equal path length the electrical conductance of the paths, as illustrated by the schematic resistors 84 and 86, and thus the magnitude of the induced currents 80 and 82, will be related to the conductivity of the blood in the respective conductivity cells 52 and 54.

The induced currents 80 and 82 flowing in the outlet and inlet conductivity cells 52 and 54 generate a changing magnetic field at the sensing location that induces a sensed current, illustrated by direction arrow 88, in the sensing coil 74. The induced currents 80 and 82 are in opposite electrical directions so that the magnetic field at the sensing location has a magnitude proportional to the difference between the induced currents. The sensed current 88 is proportional to the magnetic field at the sensing location where the sensing coil 74 encircles the second and fourth tubing branches 62 and 70, respectively. The sensed current 88 induced in the sensing transformer 74 is therefore proportional to a difference between the induced currents 80 and 82 in the outlet and inlet conductivity cells 52 and 54, respectively. The induced currents 80 and 82 in the outlet and inlet conductivity cells 52 and 54, respectively, are related to the conductivity of the fluids in those chambers. Therefore, the magnitude of the sensed current 88 induced in the sensing coil 74 will be related to the difference between the conductivities of the fluids in the outlet and inlet conductivity cells 52 and 54. The sensed current 88 is delivered to, and interpreted by a sensing logic and display circuit 90, which displays the recirculation efficiency.

It should be appreciated that the present invention will function in substantially the same way if the locations of the exciting coil 72 and sensing coil 74 are reversed.

Referring now to FIGS. 1 and 2, to use the recirculation monitor 22 to perform a recirculation test the dialysis system operator injects a bolus of a marker fluid into the treated blood in the dialyzer outlet line 32 at the needle access site 50 using a typical hypodermic needle 92. The marker fluid may have an electrical conductivity that is higher or lower than the fluid flowing in the outlet line 32. In the preferred embodiment a high conductivity marker fluid is used to avoid damaging blood cells. In the preferred embodiment the bolus is 1 milliliter of 24 percent hypertonic saline solution. The conductivity of the treated blood being returned to the patient through the dialyzer outlet line 32 and the outlet conductivity cell 52 of the recirculation monitor 22 is altered. This altered conductivity blood enters the fistula through the outlet needle 34.

If the flow balance in the fistula 26 is such that no flow is recirculating the altered conductivity blood will exit the fistula, as illustrated by the flow circulation arrow 94, without altering the conductivity of the blood within the fistula. If, however, the flow balance within the fistula 26 is such that blood is recirculating, as illustrated by flow circulation arrow 96, a portion of the blood withdrawn from the fistula 26 by the pump 36 will be the altered conductivity blood. The recirculation monitor 22 measures the conductivity of the blood flowing in the outlet line 32 and the conductivity of the blood flowing in the inlet line 30 and quantitatively determines the difference between those conductivities continuously throughout the recirculation test. The sensing logic and display circuit 90 interprets the quantitative conductivity differences measured by the recirculation monitor 22 to determine recirculation efficiency.

Figure 4:
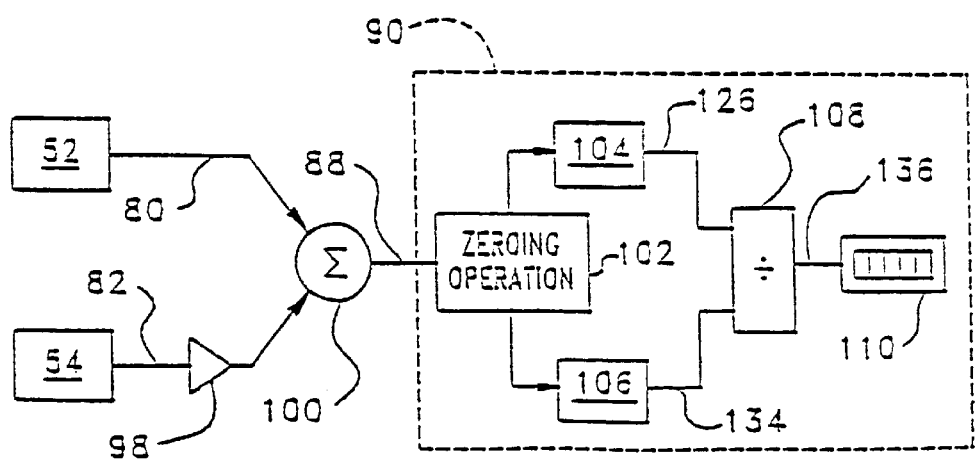
FIG. 4 is an electrical block diagram of sensing logic usable with the differential conductivity recirculation monitor illustrated in FIGS. 2 and 3.

The determination of recirculation efficiency will be explained by reference to FIGS. 4, 5 and 6. The outlet conductivity cell 52 and the inlet conductivity cell 54 may be thought of as signal generators generating the induced currents 80 and 82 in the outlet and inlet conductivity cells. The induced current 82 of the inlet conductivity cell 54 is inverted 98 and added 100 to the induced current 80 in the outlet conductivity cell 52, by virtue of the physical relationships between the conductivity cells, excitation coil 72 and sensing coil 74, to produce the sensed current 88.

The sensing logic and display circuit 90 performs a zeroing operation 102, a dialyzer outlet flow determining operation 104, and unrecirculated flow determining operation 106, and a dividing operation 108, and includes a visual display device 110, preferably a liquid crystal display. Alternatively the functions of the sensing logic and display circuit 90 may be performed by a digital computer (not shown).

Figure 5:
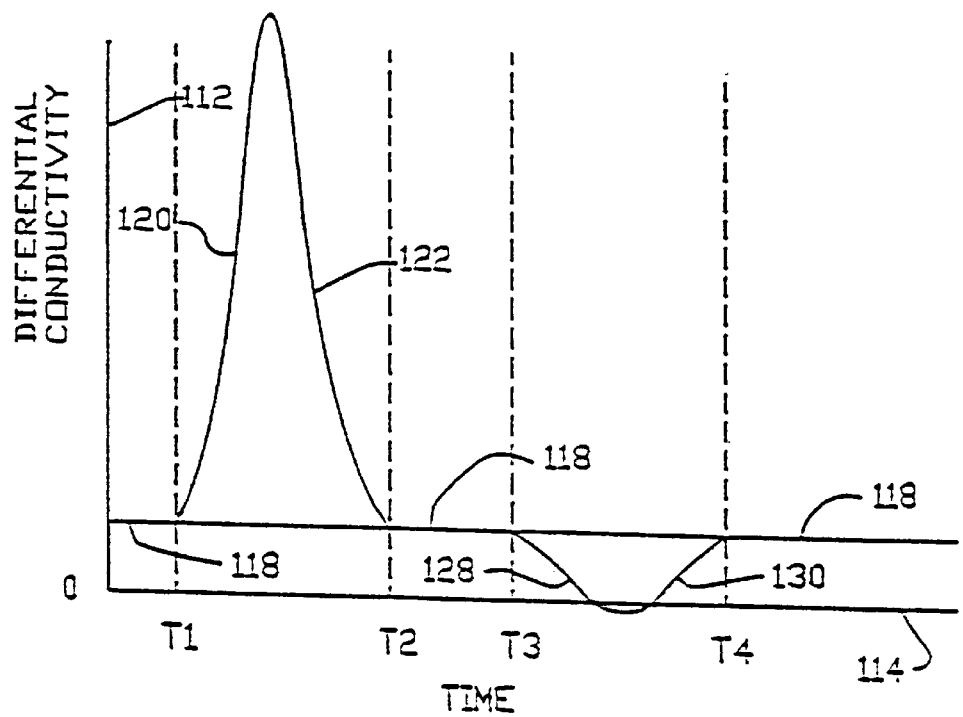
FIG. 5 is a graph illustrating differential conductivity versus time during a recirculation test employing the differential conductivity recirculation monitor shown in FIG. 2.
Figure 6:
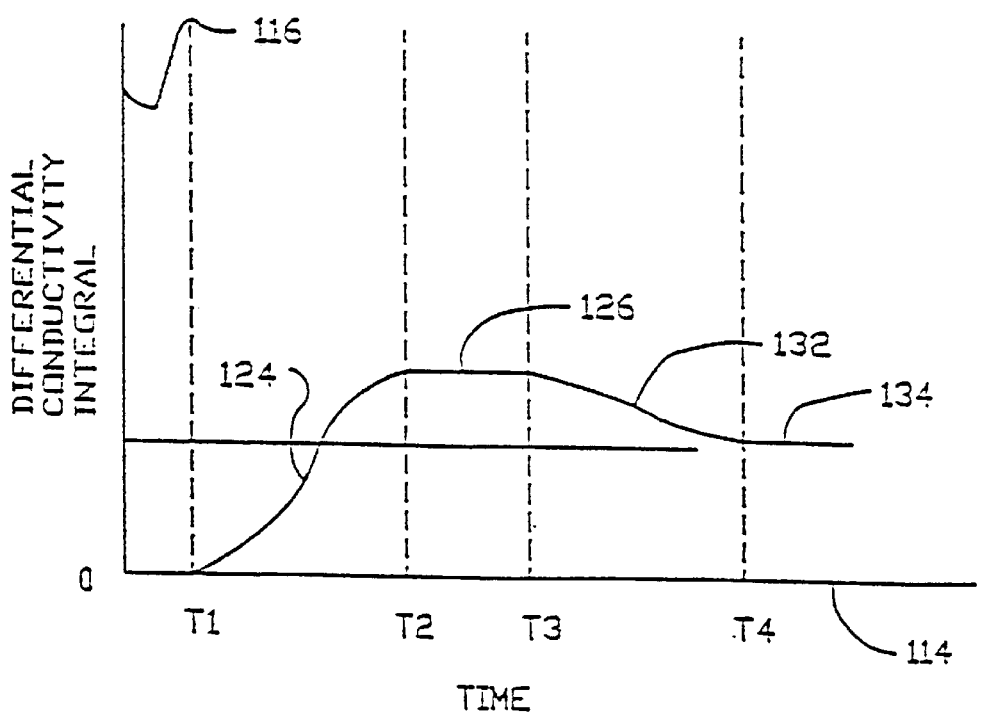
FIG. 6 is a graph illustrating the integral of differential conductivity versus time during a recirculation test employing the differential conductivity recirculation monitor shown in FIG. 2, having substantially the same time scale as FIG. 5.

FIG. 5 is a graph illustrating differential conductivity (reference 112) as a function of time (reference 114) during a typical recirculation test. FIG. 6 is a graph illustrating the integral of differential conductivity (reference 116) as a function of time 114 during the typical recirculation test. Prior to the beginning of the recirculation test there may be some normal difference (reference 118) between the conductivity of the treated blood in the dialyzer outlet line 32 (FIG. 2) and the untreated blood in the dialyzer inlet line 30 (FIG. 2). This normal conductivity difference 118 is subtracted from the sensed current 88 by the zeroing operation 102 of the sensing logic and display circuit 90 to remove the effect of the normal difference in conductivity 118 from determination of recirculation efficiency. The recirculation test begins (reference time T1) when the bolus of high conductivity fluid is injected into the dialyzer outlet line 32 (FIG. 2) at the needle access site 50 (FIG. 2). The conductivity of the treated blood in the dialyzer outlet line 32 (FIG. 2) is increased. As the bolus passes through the outlet conductivity cell 52 (FIG. 2) the differential conductivity 112 increases (reference 120) and then decreases (reference 122) until the normal conductivity difference 118 is reached (reference time T2). The outlet flow determining operation 104 calculates the integral of conductivity from the start of the test (reference time T1) until the differential conductivity returns to the normal value 118 (reference time T2). The integral 116 of the conductivity increases (reference 124) until a first steady state value (reference 126) of the integral 116 is reached when the differential conductivity 112 returns to the normal value 118 (reference time T2). The first steady state value 126 is stored by the outlet flow determining operation 104 and is representative of the flow of treated blood in the dialyzer outlet line 32 (FIG. 2).

After the treated blood with the altered conductivity enters the fistula 26 (FIG. 1) a portion of it may recirculate and be withdrawn from the fistula 26 (FIG. 1) through the dialyzer inlet line 30 (FIG. 2). The conductivity of the untreated blood in the inlet conductivity cell 54 is increased (reference time T3), causing the differential conductivity to decrease 128 and then increase 130, returning to the normal value of conductivity difference 118 (reference time T4). The integral of differential conductivity from the beginning of the recirculation test (reference time T1) until the normal value of conductivity difference 118 is reached again (reference time T4) is calculated by the unrecirculated flow determining operation 106 of the sensing logic and display circuit 90. The integral of differential conductivity 116 decreases (reference) to a second steady state value 134 (reference time T4.

The second steady state value 134 of the integral of differential conductivity is stored by the unrecirculated flow determining operation 106 of the sensing logic and display circuit 90 and is representative of the portion of the bolus of high conductivity liquid that was not recirculated. The second steady state value 134 is thus representative of the unrecirculated portion of the treated blood flow. The dividing operation divides the second steady state value 134 by the first steady state value 126 to calculate a recirculation efficiency 136. The recirculation efficiency 136 is provided to the operator as a visual output by the display device 110.

It will be apparent to those skilled in the art that the sensing logic and display circuit 90 may be implemented using analog or digital circuit devices and that other calculation algorithms may be used to calculate recirculation efficiency 138. Further, the recirculation efficiency 138 may be calculated in real time or, alternatively, the necessary data stored and the calculations performed on the stored data.

Further details of the preferred embodiment of the differential conductivity recirculation monitor will be explained by reference to FIGS. 7–11.

Figure 7:
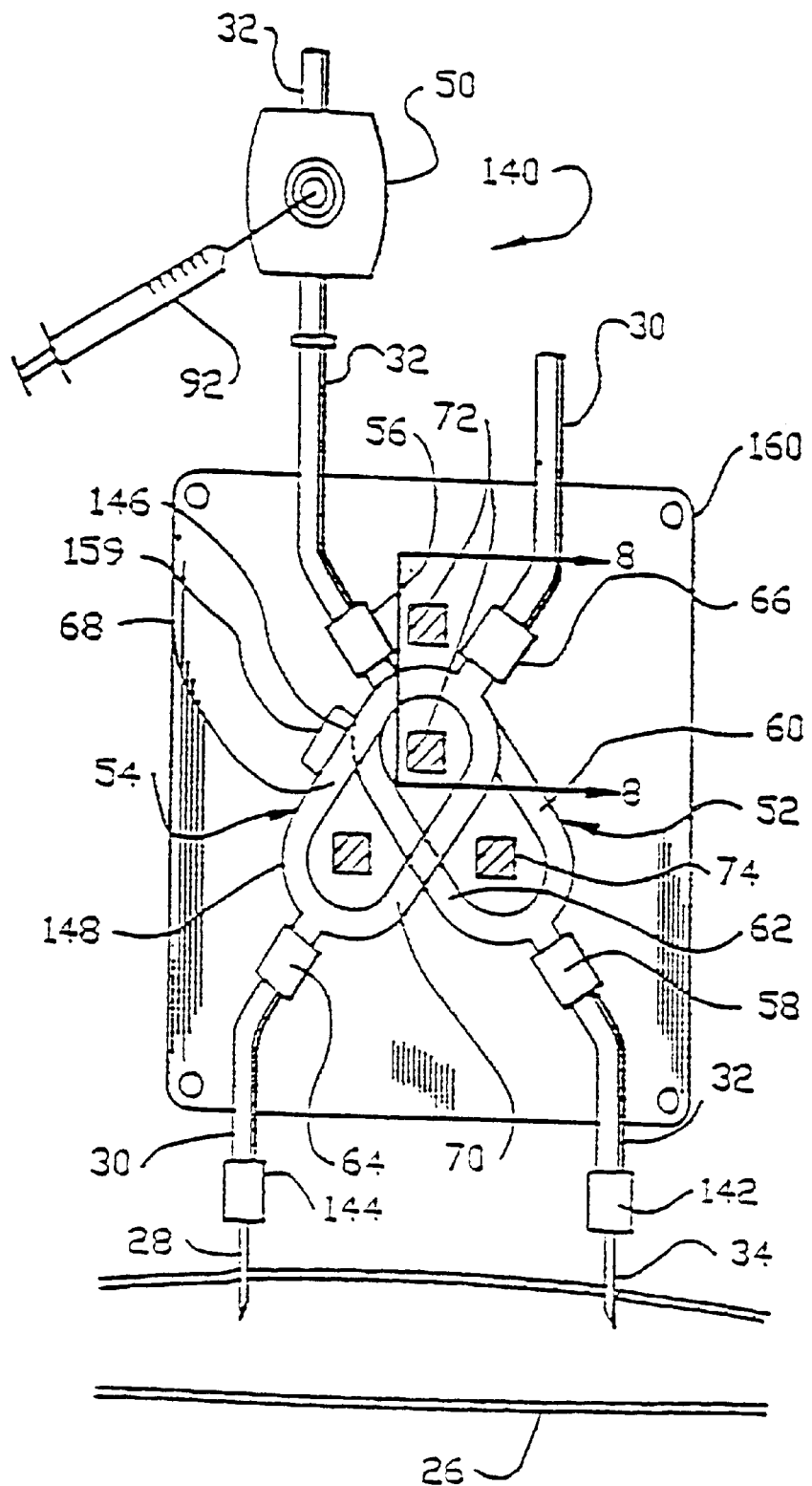
FIG. 7 is a partial elevational view of a tubing set and sectional view of an excitation and sensing unit for use with the dialysis system shown in FIG. 1, incorporating the differential conductivity recirculation monitor in accordance with the present invention.

FIG. 7 illustrates a portion of a typical disposable tubing set 140 incorporating conductivity cells 52 and 54 in accordance with the present invention. As is well known in the art, it is highly desirable for all portions of the tubing set 140 to be used with a dialysis system to be disposable, in order to prevent cross contamination and infection between patients. This is true of most blood and other biological or medical fluid processing systems.

Disposable tubing sets may be formed from a plurality of plastic tubes, connectors, needles and medical devices using techniques that are well known in the art. The discussion of the tubing set 140 will therefore be limited to a discussion of the differential conductivity recirculation monitor 22 (FIG. 1) portion of the tubing set.

The dialyzer outlet line 32 is a plastic tube which extends through the needle access site 50, into the outlet conductivity cell 52. The outlet conductivity cell 52 comprises a plastic conduit loop and includes the upstream connection 56, elongated divided first and second tubing branches 60 and 62, and the downstream connector 58. The downstream connector 58 has mounted in it an extension of the dialyzer outlet line 32, which is mounted through a connector 142 to the outlet needle 34.

The dialyzer inlet needle 28 is connected through a connector 144, to the dialyzer inlet line 30. The dialyzer inlet line 30 is connected to the inlet conductivity cell 54, which includes the upstream connection 64, elongated divided third and fourth tubing branches 68 and 70 respectively, and downstream connector 66. The dialyzer inlet line 30 extends from the downstream connector 66 to the dialyzer apparatus 24 (FIG. 1).

In the preferred embodiment the portion of the dialyzer outlet line 32 between the dialyzer outlet needle 34 and the downstream connector 58 of the outlet conductivity cell 52 and the portion of the dialyzer inlet line 30 between the dialyzer inlet needle 28 and the upstream connector 64 of the inlet conductivity cell 54 must be sufficiently long so that the bolus of marker fluid passes completely through the outlet conductivity cell before any altered conductivity fluid from the fistula 26 enters the inlet conductivity cell.

Figure 8:
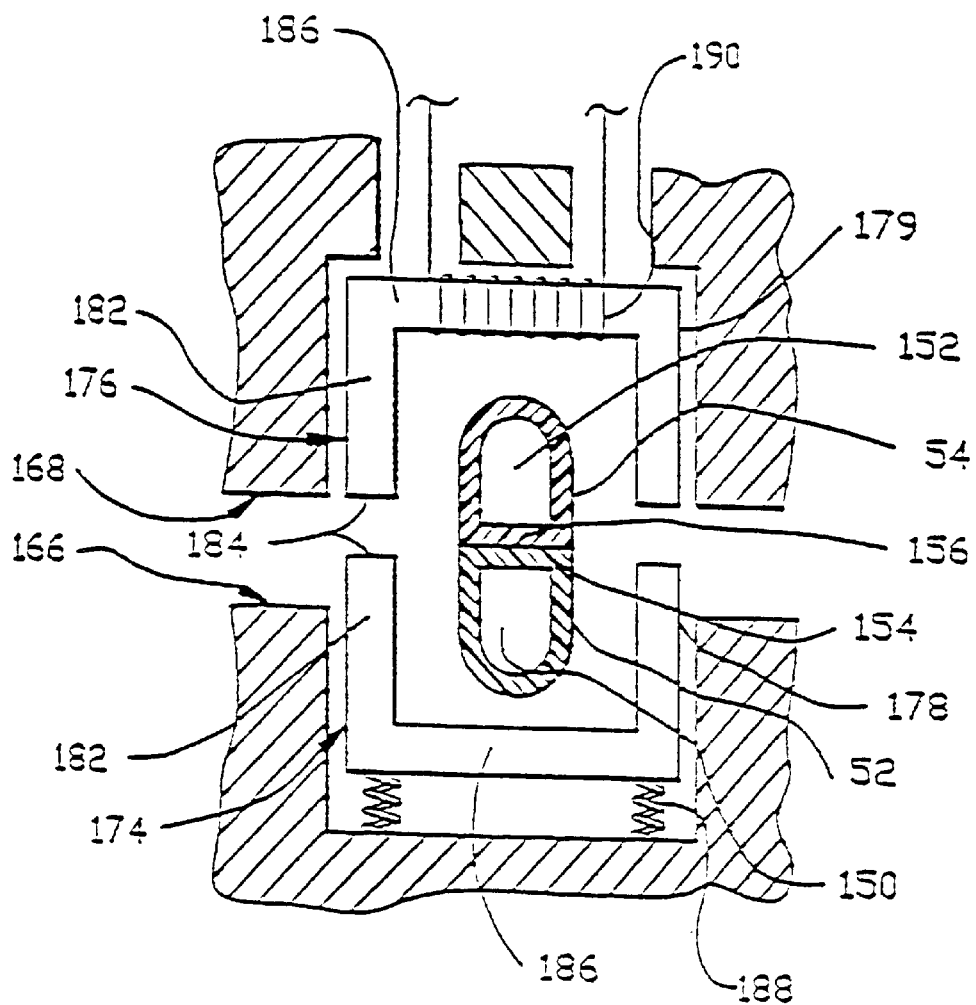
FIG. 8 is a partially diagrammatic sectional view taken substantially at line 8—8 in FIG. 7.

The conductivity cells 52 and 54 have the overall shape of links in an ordinary chain, straight side portions 146 being joined at their ends by semicircular portions 148. In cross-section at the excitation location, as shown in FIG. 8, the wall of each conductivity cell 42 and 54 defines a D, the insides of the Ds providing conduit portions 150 and 152. A flat portion 154 of the D of the outlet conductivity cell 52 is abutted and adhered to a flat portion 156 of the D of the inlet conductivity cell 54 along one pair of semicircular portions 148 of the conductivity cells. The other pair of circular portions 148 are separated so that axes of the conductivity cells 52 and 54 define therebetween an angle of approximately sixty degrees. The flat portions 154 and 156 of the conductivity cells 52 and 54 are further joined along two of the straight portions 146 at a location along the second and fourth tubing branches 62 and 70, respectively at the sensing location. An orientation tab 159 is formed on the inlet conductivity cell 54.

Figure 9:
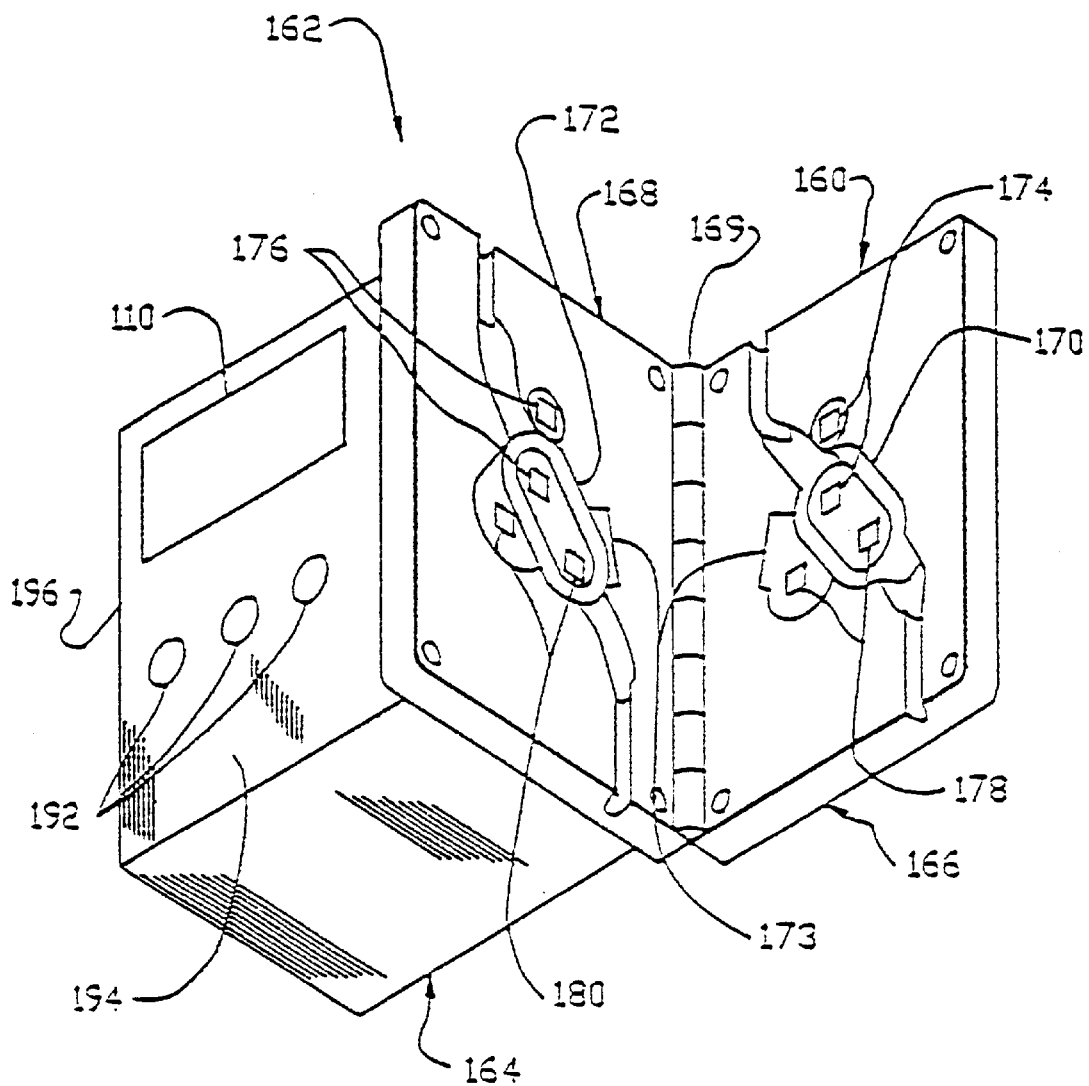
FIG. 9 is a partially diagrammatic perspective view of the excitation and sensing unit of the differential conductivity recirculation monitor of the present invention.

Mating with tube set 140 is a tubing set acceptor 160. As shown in FIG. 9, the tubing set acceptor 160 comprises a portion of an excitation and sensing unit 162 which also includes a logic circuit module 164. The tubing set acceptor 160 comprises a portion of a first, or rear, acceptor plate 166 and a second, or front, acceptor plate 168 joined by a hinge 169 for motion between open and closed positions and provided with a latch or spring (not shown) to hold the acceptor plates in the closed position. The first acceptor 166 plate is relieved to accept into appropriately-shaped indentations 170 thereof the outlet conductivity cell 52 (FIG. 2) and portions the tubing set 140 (FIG. 7). The second acceptor plate 168 is relieved to accept into appropriately-shaped indentations 172 thereof the inlet conductivity cell 54 and portions of the tubing set 140 (FIG. 7). An orientation tab recess 173 is defined by at least one of the appropriately shaped indentations 170 and 172. The orientation tab recess 173 cooperates with the orientation tab 159 (FIG. 7) of the tubing set 140 (FIG. 7) to assure that the tubing set is correctly oriented when installed in the tubing set acceptor 160.

The tubing set acceptor 160 is sufficiently large to support the conductivity cells 52 and 54 and enough of the dialyzer outlet line 32 and dialyzer inlet line 30 so that fluid flow patterns through the conductivity cells are substantially repeatable, being relatively unaffected by bends, curves, tubing movement, and other disturbances or variations in the positions of the outlet and inlet lines with respect to the conductivity cells during measurement.

The excitation coil 72 and sensing coil 74 are mounted to the tubing set acceptor 160. The excitation coil 72 and sensing coil, 74 are positioned at right angles to each other to minimize magnetic interference between the coils. The excitation coil 72 comprises a first, or rear, and a second, or front, half core 174 and 176, respectively. Similarly the sensing coil comprises a third, or rear, and a fourth, or front, half-core 178 and 180 respectively. The first and third half-cores 174 and 178, respectively are mounted to the first acceptor plate 166 and the second and third half cores 176 and 180 respectively are mounted to the second acceptor plate 186.

As illustrated in FIG. 8, each half core has a U-shaped configuration, with short legs 162 having ends 184 and connecting legs 186. The tubing set acceptor 160 holds a portion of the tubing set 140 which includes the conductivity cells 52 and 54 in a fixed relationship with the excitation coil 72 and sensing coil 74.

The first and second half cores 174 and 176 are oriented so that their ends 184 abut when the first and second acceptor plates 166 and 166 are brought to the closed position. The excitation coil 72 thus formed is in the shape of a rectangle defining a rectangular window. The third and fourth half cores 178 and 180 are similarly oriented so that their ends abut when the first and second acceptor plates 166 and 168 are brought to the closed position. The sensing coil 74 thus formed is also in the shape of a rectangular ring defining a rectangular window (not shown). When a tubing set 140 is placed in the tubing set acceptor 160 the first and third tubing branches 60 and 68 are engaged in the window of the excitation coil 72 and the second and fourth tubing branches 62 and 70 are engaged in the window of the sensing coil 74 so that the coils encircle the corresponding tubing branches. Biasing springs 188 may be provided to hold corresponding half-cores in firm contact when the acceptor plates 166 and 168 are closed.

The legs 182 and 186 of the coil 72 and 74 are square in cross-section. At least one connecting leg 186 of each coil 72 and 74 is transformer wire wrapped 190.

The logic circuit module 164 of the excitation and sensing unit 162 may be mounted to one of the acceptor plates 168 or may be separate from the tubing set acceptor 160 with wiring interconnections (not shown) to the tubing set acceptor 160. Further, either or both of the logic circuit module 164 or the tubing set acceptor 160 may be incorporated into the dialysis apparatus 24. The logic circuit module houses the sensing logic and display circuit 90, with the display device 110 and one or more manual input switches 192 to enable the operator to perform such functions as turning the recirculation monitor on and off, testing the operation of the monitor and initiating recirculation test, and may also include switches and displays associated with other hemodynamic monitoring functions.

Although the display device 110 and manual input switches 192 are shown in FIG. 9 as being on a side 194 of the logic circuit module 164 adjacent to the second acceptor plate 168, in the preferred embodiment the display device and manual input switches may be on a side 196 opposite the second acceptor plate 168, or any other side of the logic circuit module.

The circuitry for conductivity measurement and calibration may suitably be as set forth in the Ogawa patent incorporated by reference above.

The apparatus and methods described above may optionally be adapted to measure and detect other hemodynamic parameters such as the presence of entrained air in the treated blood returned to the patient from the dialysis apparatus 24 through the dialyzer outlet line 32. For this use it is not necessary to inject saline at the needle access site 50. Entrained air in the blood in the form of a large bubble will cause an electrical discontinuity in the outlet conductivity cell 52 as it passes through either of the tubing branches 60, 62 of the outlet conductivity cell 52. This will cause the magnitude of induced current 80 flowing in the outlet conductivity cell 52 to be greatly reduced or turned off completely, depending on the size of the bubble. Further, a plurality of small bubbles will effectively reduce the conducting volume of the blood in the tubing branches 60, 62 of the conductivity cell, decreasing the conductance, and therefore the induced current 80, in the outlet conductivity cell 52.

By sensing this reduction in the outlet conductivity cell 52 induced current 80 the passage of a bubble or a plurality of bubbles can be detected, and corrective action taken, if necessary, to minimize their introduction into the patient through the outlet line 32 and outlet needle 28. Corrective action may include turning off the dialysis apparatus 24, closing a venous clasp (not shown) and/or activating indicator or alarm devices to alert a human operator of the presence of the air bubble of bubbles.

In the preferred embodiment, a difference in the conductivity of the blood in the outlet conductivity cell 52 of the outlet line 32 and the blood in the inlet conductivity cell of the inlet line 30 is substantially constantly monitored. When one or more air bubbles enter the outlet conductivity cell 52, causing the conductance, and thus the induced current 80 and resulting sensed conductivity of the fluid in the cell 52, to decrease relative to the conductivity of the blood in the inlet conductivity cell 54, this decrease is sensed by logic in the sensing logic and display circuit 90 of the logic circuit module 164 of the excitation and sensing unit 162. If the conductivity of the blood in the outlet conductivity cell 52 is sufficiently lower than the conductivity of the blood in the inlet conductivity cell 54, this conductivity difference is interpreted as the presence of entrained air in the outlet line 32.

The apparatus and methods described above may optionally be adapted to measure the hemodynamic parameter of blood volumetric flow in the outlet line 32. Blood volumetric flow rate may be measured and displayed as an incident to the measurement of a degree of recirculation, as described above, or may be measured in a separate blood volumetric flow monitoring procedure.

The measurement of blood volumetric flow using the differential conductivity sensor of the present apparatus will be explained by reference to FIGS. 10 and 11. The conductivity of a fluid is directly proportional to the concentration of conductivity producing ions in the fluid. Consider an ideal bolus 202 of hypertonic saline solution having a known volume vol and a known mass of conductivity altering ions M. The ion concentration of this ideal bolus 202 would be:

$$C = \frac{M}{vol} \qquad \text{(Equation 2)}$$

If this bolus were injected at the needle access site 50 into the outlet line 32, which is a tube of known cross-sectional area a, into fluid flowing at a flow rate Q, corresponding to a velocity V, the ideal bolus would pass through the outlet line 32 in the form of a cylinder having a length L, L being defined as:

$$L = \frac{vol}{a} \qquad \text{(Equation 3)}$$

As this ideal bolus 202 passes through the outlet conductivity cell 52 it would cause the conductivity cell to sense a square pulse 204 of altered differential conductivity having a magnitude proportional to the ion concentration C of the bolus and a duration $t_1$ proportional to the length L of the bolus 202 and the flow rate Q of the fluid. The flow rate of the fluid can then be calculated as:

$$Q = Va = \frac{La}{t_1} = \frac{M}{Ct_1} \qquad \text{(Equation 4)}$$

Note that $Ct_1$ is the area under the sensed square pulse 204.

In reality the bolus 202' of known volume vol and known mass of conductivity altering ions M will not take the form of a perfect cylinder, but will exhibit gradual Leading edge curve 206 and trailing edge curve 209, and will further diffuse into the fluid in the outlet line 32. The differential conductivity pulse 204' caused by the passage of the bolus 202' through the outlet conductivity cell 52 will deviate substantially from a square pulse and will have gradually increasing and decreasing leading and trailing edges 210, 212 corresponding to the leading and trailing edges 206, 208 of the bolus. Furthermore, the time $t_2$ that the bolus 202' takes to pass through the outlet conductivity cell will be longer than the time $t_1$ for an ideal bolus 202. In order to determine the flow rate, Q it is necessary to determine the area under the differential conductivity curve by integrating the output over time as follows:

$$Q = \frac{M}{\int_0^{t_2} C(t) dt} \qquad \text{(Equation 5)}$$

Thus, if a bolus of saline of a known volume vol and a known concentration of conductivity altering ions $C_k$ is injected into the needle access site 50, the flow rate of the fluid can be determined to be:

$$Q = \frac{C_k * vol}{\int_0^{t_2} C(t) dt} \qquad \text{(Equation 6)}$$

When the fluid flowing in the conductivity cell 32 has a background conductivity, representing a background concentration $C_b$ of conductivity, measured by the outlet conductivity cell 52 immediately prior to the passage of the bolus 202' through the cell 52, representing a background level of conductivity producing ions, the effect of the background level must be subtracted to obtain the correct value of flow:

$$Q = \frac{(C_k - C_b) * vol}{\int_0^{t_2} (C(t) - C_b) dt} \qquad \text{(Equation 7)}$$

In the differential conductivity cell 22 of the preferred embodiment $C_b$ is representative of a difference in background concentration, and hence conductivity, between the fluid in the outlet conductivity cell. 52 and the fluid in the inlet conductivity cell. If, under steady state conditions, the conductivity of fluid in the outlet cell. 52 is the same as the conductivity in the inlet cell, then the background concentration $C_b$ is zero. The preferred embodiment of the present invention may optionally be provided with selectably engageable logic to analyze a differential conductivity pulse from the bolus 202' of saline passing through the outlet conductivity cell 52 and generate a value indicative of the flow rate through the conductivity cell. This value may be selectively displayable on the same display device 110 as is used to display a degree of recirculation. The bolus of saline 202' may optionally be the same bolus used to determine a degree of recirculation, in which case the flow rate will be determined substantially simultaneously with the degree of recirculation and displayed simultaneously of sequentially therewith.

The apparatus and methods described above may optionally be further adapted to incorporate the capability of measuring or detecting more than one hemodynamic parameter into a single differential conductivity measuring apparatus.

The preferred embodiments of the present invention been described by reference to determination of recirculation efficiency in a surgically created blood access site during, or in conjunction with, a hemodialysis procedure. It should be understood that the present invention is not so limited. The present invention may be used in a variety of medical and non-medical circumstances where it is desirable to determine recirculation efficiency. Further, it should be understood that the present invention may be used in a variety of medical and non-medical circumstances where it is desirable to compare the electrical conductivities of two fluids. Presently preferred embodiments of the present invention and many of its aspects, features and advantages have been described with a degree of particularity. It should be understood that this description has been made by way of preferred example, and that the invention is defined by the scope of the following claims.

What is claimed is:

1. A method for quantitatively determining a degree of recirculation flow in a vessel of a first fluid having a first electrical conductivity relative to a second fluid having a corresponding second electrical conductivity, comprising:

altering the electrical conductivity of the first fluid;

inducing first electrical current in the first fluid and a second electrical current in the second fluid, said first current generating a first electromagnetic field and said second current generating a second electromagnetic field;

sensing the difference between the first and second electromagnetic fields at sensing location after the conductivity of the first fluid is altered; and interpreting the difference between the first and second electromagnetic fields to quantitatively determine the degree of recirculation flow.

2. A method as defined in claim 1 wherein: the step of altering the electrical conductivity of the first fluid further comprises:

injecting a marker fluid having a conductivity different from the conductivity of the first fluid into the first fluid.

3. A method as defined in claim 1 wherein the step of sensing the difference of the first and second electromagnetic fields further comprises:

flowing the first fluid through a first conduit, said first conduit comprising a first conductivity cell with a continuous path configuration; and wherein said inducing step further comprises inducing the first electrical current in the first fluid in the first conductivity cell following the continuous path configuration.

4. A method as defined in claim 3 wherein: the inducing step further comprises:

positioning an exciting electromagnetic coil in proximity with the first conductivity cell at an inducing location; and inducing the first electrical current in an electrical direction along the continuous path of the first conductivity cell; and the sensing step further comprises:

positioning a sensing electromagnetic coil in proximity with the first conductivity cell at a sensing location.

5. A method as defined in claim 1 wherein the interpreting step further comprises compensating for the effect of the first conductivity of the first fluid.

6. A method as defined in claim 1 wherein the step, of sensing the difference of the first and second electromagnetic fields further comprises:

flowing the second fluid in a second conduit, the second conduit having a second conductivity cell with a continuous configuration and wherein the inducing step further comprises:

inducing the second electrical current in the second fluid in the second conductivity cell following the continuous path configuration.

7. A method as defined in claim 6 wherein the interpreting step further comprises compensating for the effects of the first conductivity of the first fluid and the second conductivity of the second fluid.

8. A method as defined in claim 1 wherein the step of sensing the difference of the first and the second electromagnetic fields further comprises:

flowing the first fluid through a first conduit, said first conduit comprising a first conductivity cell with a first continuous path configuration;

flowing the second fluid through a second conduit, said second conduit comprising a second conductivity cell with a second continuous path configuration;

wherein said inducing step includes inducing a first electrical current in the first fluid in the first conductivity cell and inducing a second electrical current in the second fluid in the second conductivity cell;

wherein said sensing step includes sensing the difference between the first electromagnetic field of the first fluid in the first conductivity cell and the second electromagnetic field of second fluid in the second conductivity cell; and producing a signal representative of the difference of the first and second electromagnetic fields of the first and the second fluids.

9. A method as defined in claim 8 wherein: the inducing step further comprises:

positioning an exciting electromagnetic coil in proximity with the first and second conductivity cells at an inducing location;

inducing the first electrical current in an electrical direction along the first continuous path of the first conductivity cell; and simultaneously inducing the second electrical current to flow in the same electrical direction along the second continuous path of the second conductivity cell as the direction of the first electrical current; and the sensing step further comprises:

positioning a sensing electromagnetic coil in proximity with the first and second conductivity cells at a sensing location with the first conductivity cell oriented at the sensing location with the first electrical current disposed in an opposite electrical direction from the electrical direction of the second electrical current.

10. A method as defined in claim 8 wherein: the step of altering the electrical conductivity of the first fluid further comprises:

injecting a marker fluid having a conductivity different from the conductivity of the first fluid into the first fluid.

11. An apparatus for quantitatively determining a degree of recirculation flow of a first fluid in a vessel, said first fluid having a first electrical conductivity relative to a second fluid having a corresponding second electrical conductivity, comprising:

means for altering the electrical conductivity of the first fluid; and means for inducing a first electrical current in the first fluid and a second electrical current in the second fluid, said first current generating a first electromagnetic field and said second current generating a second electromagnetic field;

means for sensing the difference between the first and second electromagnetic fields after the conductivity of the first fluid is altered; and means for interpreting the difference between the first and second electromagnetic fields to quantitatively, determine the degree of recirculation flow.

12. An apparatus as defined in claim 11 wherein:

the means for altering the electrical conductivity of the first fluid further comprises:

means for injecting a marker fluid having an electrical conductivity different from the first conductivity of the first fluid into the first fluid.

13. An apparatus as defined in claim 11 wherein the means for sensing the difference of the electromagnetic fields of the first fluid and the second fluid further comprises:

a first conduit through which the first fluid flows to the vessel, said first conduit comprising a first conductivity cell with a first conductivity cell upstream connection, a first conductivity cell downstream connection, and two branches connecting the upstream connection to the downstream connection with a continuous path configuration from the upstream connection to the downstream connection through one of the two branches and returning to the upstream connection through the other one of the two branches;

means for inducing a first electrical current in the first fluid in the first conductivity cell following the continuous path configuration.

14. An apparatus as defined in claim 13 wherein:

the inducing means comprises an exciting electromagnetic coil disposed in proximity with the first conductivity cell at an exciting location; and the sensing means comprises:

a sensing electromagnetic coil disposed in proximity with the first conductivity cell at a sensing location.

15. An apparatus as defined in claim 11 wherein the and means for interpreting further comprises means for compensating for the effect of the first conductivity of the first fluid.

16. An apparatus as defined in claim 11 wherein the means for sensing the difference of the first and second electromagnetic fields further comprises:

a second conduit through which the second fluid having the second conductivity flows, the second conduit having a second conductivity cell with a second continuous configuration wherein the means for inducing further comprises:

means for inducing the second electrical current in the second fluid in the second conductivity cell following the second continuous path configuration.

17. An apparatus as defined in claim 16 wherein the means for sensing the difference of the first and the second electromagnetic fields further comprises:

a first conduit through which the first fluid flows to the vessel, said first conduit comprising a first conductivity cell with a first conductivity cell upstream connection, a first conductivity cell downstream connection, and two branches connecting the upstream connection to the downstream connection with a first continuous path configuration from the upstream connection to the downstream connection through one of the two branches and returning to the upstream connection through the other one of the two branches;

a second conduit through which the second fluid flows from the vessel, said second conduit comprising a second conductivity cell with a second conductivity cell upstream connection, a second conductivity cell downstream connection, and two branches connecting the upstream connection to the downstream connection with a second continuous path configuration from the upstream connection to the downstream connection through one of the two branches and returning to the upstream connection through the other one of the two branches;

wherein said means for inducing includes including a first electrical current in the first fluid in the first conductivity cell and inducing a second electrical current in the second fluid in the second conductivity cell;

wherein said means for sensing includes sensing the difference between the first electromagnetic field the first fluid in the first conductivity cell and the second electromagnetic field of the second fluid flowing in the second conductivity cell, and means for producing a signal representative of the difference the first and second electromagnetic fields of the first and the second fluids.

18. An apparatus as defined in claim 17 wherein: the means for altering the electrical conductivity of the first fluid further comprises:

means for injecting a marker fluid having an electrical conductivity different from the first conductivity of the first fluid into the first fluid.

19. An apparatus as defined in claim 17 wherein:

the inducing means her comprises an exciting electromagnetic coil disposed in proximity with the first and second conductivity cells at an exciting location, the first conductivity cell being oriented at the exciting location with respect to the second conductivity cell with first electrical current in a first electrical direction with respect to the exciting electromagnetic coil along the first continuous path of the first conductivity cell and the second electrical current in a second electrical direction along the second continuous path of the second conductivity cell which is the same electrical direction with respect to the exciting electromagnetic coil as the direction of the first electrical current; and the sensing means further comprises a sensing electromagnetic coil disposed in proximity with the first and second conductivity cells at a sensing location, the first conductivity cell being oriented at the sensing location with respect to the second conductivity cell with the electrical direction of the first electrical current with respect to the sensing electromagnetic coil disposed opposite the second electrical direction of the second electrical current with respect to the sensing electromagnetic coil.

20. An apparatus as defined in claim 11 further comprising an apparatus adapted for interpreting the difference between the first and second electromagnetic fields for quantitatively determining degree of flow recirculation within a vessel.

* * * * *

UNITED STATES PATENT AND TRADEMARK OFFICE
CERTIFICATE OF CORRECTION

PATENT NO.   : 6,452,371 B1
DATED        : September 17, 2002
INVENTOR(S)  : James M. Brugger It is certified that error appears in the above-identified patent and that said Letters Patent is hereby corrected as shown below:

<u>Title page,</u>
Item [75], should read:

-- Inventors:   James M. Brugger, Newburyport, MA (US)
                Francis T. Ogawa, Lakewood, CO (US)
                George W. Buffaloe IV, Arvada, CO (US) --

Signed and Sealed this

First Day of July, 2003

JAMES E. ROGAN
*Director of the United States Patent and Trademark Office*